(12) United States Patent
Edwards et al.

(10) Patent No.: US 8,672,826 B2
(45) Date of Patent: Mar. 18, 2014

(54) VIVO STIMULATION OF CELLULAR MATERIAL

(75) Inventors: Jeffrey David Edwards, Claremont (AU); Chin Joo Goh, Singapore (SG); Kay Fei Chan, Singapore (SG)

(73) Assignee: Global Energy Medicine Pty. Ltd. (AU)

( * ) Notice: Subject to any disclaimer, the term of this patent is extended or adjusted under 35 U.S.C. 154(b) by 745 days.

(21) Appl. No.: 12/296,385

(22) PCT Filed: Apr. 4, 2007

(86) PCT No.: PCT/AU2007/000454
§ 371 (c)(1),
(2), (4) Date: May 21, 2010

(87) PCT Pub. No.: WO2007/115362
PCT Pub. Date: Oct. 18, 2007

(65) Prior Publication Data
US 2010/0261947 A1    Oct. 14, 2010

(30) Foreign Application Priority Data
Apr. 7, 2006    (AU) ................................ 2006901819

(51) Int. Cl.
*A61N 1/00*    (2006.01)
(52) U.S. Cl.
USPC ........ 600/13; 600/9; 600/10; 600/11; 600/12; 600/14; 600/15; 435/173.1; 607/46; 607/50; 607/68
(58) Field of Classification Search
USPC ............. 600/9–15; 435/173.1; 607/46, 50, 68
See application file for complete search history.

(56) References Cited

U.S. PATENT DOCUMENTS

| | | | |
|---|---|---|---|
| 3,794,022 A | | 2/1974 | Nawracaj et al. |
| 3,890,953 A | * | 6/1975 | Kraus et al. .................... 600/14 |
| 3,952,751 A | * | 4/1976 | Yarger .......................... 607/71 |
| 3,983,881 A | | 10/1976 | Wickham |
| 4,105,017 A | | 8/1978 | Ryaby et al. |
| 4,266,532 A | * | 5/1981 | Ryaby et al. .................... 600/14 |
| 4,326,534 A | | 4/1982 | Axelgaard et al. |
| 4,338,945 A | | 7/1982 | Kosugi et al. |
| 4,535,775 A | * | 8/1985 | Brighton et al. ................ 607/51 |
| 4,620,543 A | | 11/1986 | Heppenstall et al. |
| 4,922,908 A | | 5/1990 | Morawetz et al. |

FOREIGN PATENT DOCUMENTS

| | | |
|---|---|---|
| SU | 554870 | 4/1977 |
| SU | 865299 | 9/1981 |

OTHER PUBLICATIONS

Derwent Abstract Accession No. A3701A/02, Class P34, SU 554870 A (Riga Traurmatology), May 23, 1977 (1 page) and translation from Russian (pp. 1-4).
Derwent Abstract Accession No. A84-105311/17, Class P34, SU 865299 (Mikhailichenko), Sep. 25, 1981.

* cited by examiner

*Primary Examiner* — Christine Matthews
*Assistant Examiner* — Sunita Reddy
(74) *Attorney, Agent, or Firm* — Alston & Bird LLP

(57) ABSTRACT

The present invention relates to the in vivo stimulation of cellular material. In particular, the present invention relates to a method for stimulating cells and tissue in vivo comprising the step of applying to said cells and tissue an electrobiomimetic stimulus, wherein the growth characteristics of said cells and tissue are enhanced as compared to cells and tissue not receiving said stimulus.

15 Claims, 16 Drawing Sheets

1.1 Heel Strike      1.2 Mid Stance      1.3 Lift Off 1.4

2.1 Walk – 1.5 x BW - 1.0 Cycles per second 2.2 Jog – 2.0 x BW - 1.8 Cycles per second 2.3 Run – 3.5 x BW – 2.3 Cycles per second

VIVO STIMULATION OF CELLULAR MATERIAL

FIELD OF THE INVENTION

The present invention relates to the in vivo stimulation of cellular material. In particular, the present invention relates to a method for stimulating cells and tissue in vivo comprising the step of applying to said cells or tissue a stimulus which promotes cellular activity.

BACKGROUND OF THE INVENTION

Use of electromagnetic field pulses (EMFP) for the treatment of chronic disorders like arthritis, tendonitis and inflammation are well known. See, for example, U.S. Pat. Nos. 5,376,065, 4,266,532, 4,461,663, 4,535,775, 3,890,953, 3,893,462, 3,952,751 and 4,667,809. In some of these previously described methods, a section of the body to be treated, such as a limb, is placed inside an annular coil. EMFP are then applied within clinically usable frequencies in order to produce endogenous regeneration by stimulating cartilage and/or connective tissue. See, for example, U.S. Pat. Nos. 3,270,746, 3,329,149 and 3,952,751. It is to be understood that the above described methods are reflective of the efforts in the prior art to employ bursts of EMFP in the megahertz range, as opposed to other efforts in the prior art, which employ bursts of pulses of electromagnetic waves which are in the kilohertz range or lower.

In the past ten years, relatively high frequency EMFP has been used in the treatment of various disorders (see, for example, U.S. Pat. Nos. 4,454,882, 4,674,482, 4,998,532 and 5,014,699). Also in recent years the clinical use of EMFP at radio frequencies has been used. In these areas pulse bursts having sinusoidal or other form have been used. The frequency used is often around 27 MHz with each pulse burst typically exhibiting a width of sixty-five microseconds and containing a range of 1,100 to 10,000 pulses per burst, and with a pulse burst repetition rate in the range of 0.01 to 1,000 Hertz.

However, while there has been a large amount of research in the use of EMFP for the treatment of a number of disorders, there still remains a high degree of uncertainty regarding the most effective parameters that can be used for treatment. This is illustrated by the numerous patents reflect the plethora of possible parameters that have been trialled (see, U.S. Pat. No. 4,467,808 which utilizes a 20-100 KHz signal generated by an alternating current power supply for the treatment of osteoporosis in bone; U.S. Pat. Nos. 4,266,532 and 4,461,663 which describe the use of unidirectional low voltage pulses; and U.S. Pat. No. 4,535,775, which describes a non-invasive capacitor-coupled signal.

Consequently, it can be seen that there remains a continuing need for a therapeutic regime for the use of EMFP in vivo that correctly identifies clinically useful parameters.

SUMMARY OF THE INVENTION

The inventors have shown that by the application of exogenous EMFP, which mimics the effects of real physical exercise, it is possible to treat cells, tissue and organs in situ. In particular, the inventors have determined specific electrobiomimetic stimuli that equate to real physiological conditions associated with exercise.

Accordingly, in a first aspect the present invention provides a method for stimulating cells and tissue in vivo comprising the steps of:

selecting a pattern of specifically configured time varying EMFP signals according to the type of physical exercise and the associated bioelectrical effects produced by cells and tissue during exercise desired to be mimicked; and
applying to said cells and tissue an electrobiomimetic stimulus comprising the selected time varying EMFP signals;
wherein the growth characteristics of said cells and tissue are enhanced as compared to cells and tissue not receiving said stimulus.

In a second aspect, the present invention provides a method for stimulating cells and tissue in vivo comprising the steps of:

selecting a pattern of specifically configured time varying EMFP signals according to the type of physical exercise and associated bioelectrical effects produced by cells and tissue during exercise desired to be mimicked; and,
applying to said cells and tissue an electrobiomimetic stimulus comprising the signal pattern, said signal pattern comprising a plurality of time periods, wherein each time period is associated with a type of physical exercise and comprises a plurality of electromagnetic field pulse blocks separated by intervals of no electromagnetic field pulses, each electromagnetic field pulse block comprises a plurality of electromagnetic field pulses of defined duration, wherein each electromagnetic field pulse of the plurality of electromagnetic field pulses is separated by a time variable pulse space and wherein said intervals vary in length of time between each period and wherein the duration of the electromagnetic pulses are uniform.

Preferably, the electrobiomimetic stimulus comprises between 2 and 4 time periods, more preferably between 2 and 3 time periods and most preferably three time periods, wherein each time period comprises blocks of electromagnetic field pulse, which are distinct from each other. It will be appreciated by those skilled in the art that the periods are designed to mimic the typical exercise pattern of "warm up", "maximal exercise" and "cool down". In some embodiments, the time periods simulating a gentle walk (period 1), explosive exercise (period 2) and then light jog (period 3), wherein the rate or frequency of delivery of the blocks of electromagnetic field pulse plays an important role. Accordingly, the duration of each time period will be tailored to the desired result and to mimic the exercise pattern outlined above. In some embodiments, the electrobiomimetic stimulus comprises three time periods, wherein time period 1 has duration of between 2 minutes and 9 minutes, time period 2 has duration between 10 minutes and 18 minutes and time period 3 has duration between 6 minutes and 12 minutes.

It will be appreciated that as the duration of each time period varies the number of electromagnetic field pulse blocks or "patterns" within each time period will also vary. The electromagnetic field pulse blocks are designed to replicate the piezo-electric response observed in fully hydrated connective tissues, when subjected to normal physiological stress levels. Each electromagnetic field pulse block is separated by an interval of no electromagnetic field pulse. The interval separating the electromagnetic field pulse blocks will be of variable time lengths depending upon the treatment requirements. In some embodiments, the interval between each electromagnetic field pulse block in period 1 will be between 14 ms and 200 ms, while the interval in period 2 will be between 5 ms and 80 ms and the interval in period 3 between 20 ms and 100 ms.

It will be appreciated by those skilled in the art that within each electromagnetic field pulse block, there will be a plurality of individual electromagnetic field pulses. Each electromagnetic field pulse provides growth altering characteristics to cells and tissue in vivo. As such, any magnetic field intensity may be used as long as it provides growth altering characteristics to cells and tissue. In some embodiments, the magnetic field intensity used is between 1 Gauss to 100 Gauss i.e. between 0.0001 T to 0.01 T. Preferably, the magnetic field intensity is between about 1 Gauss to 100 Gauss, more preferably 3 Gauss. It will be appreciated that this may also be expressed in the terms of mV per cm. In this instance, the preferred intensity is 1.3 mV per cm.

As discussed above, the electromagnetic pulse blocks replicate the piezo-electric response to fully hydrated connective tissues. As such, the duration of each electromagnetic field pulse can vary. Preferably, the pulse duration is between 20 µs and 380 µs.

Within each electromagnetic pulse block there is a plurality of electromagnetic field pulses. Preferably, the number of electromagnetic field pulses in each block is between 1 and 50, preferably, between 10 and 30, most preferably about 20. In some embodiments, the number of electromagnetic field pulses within each block is 20 and the pulse duration for each pulse is about 100 µs.

Each electromagnetic field pulse within each block can be spaced by varying time spaces. Typically, the time space between each electromagnetic field pulse is between 0 and 300000 µs. In some preferred embodiments, the 20 electromagnetic field pulses have spacings of P1—1 to 25500 µs; P2—0 to 24000 µs; P6—0 to 20000 µs; P7—0 to 20000 µs; P8—0 to 2000; P9—0 to 22000 µs; P10—0 to 24000 µs; P11—0 to 25500 µs; P12—0 to 24000 µs; P13—0 to 22000 µs; P14—0 to 22000 µs; P15—0 to 24000 µs; P16—0 to 12000 µs; P17—0 to 15000 µs; P18—0 to 20000 µs; P19—0 to 21000 µs and P20—0 to 22000 µs.

In a third aspect the present invention provides a method for treating tissue in situ comprising:
(i) collecting a selected portion of tissue;
(ii) securing said portion of tissue adjacent to an energy transmitting element;
(iii) selecting a pattern of specifically configured time varying EMFP signals according to the type of physical exercise and the associated bioelectrical effects produced by cells and tissue diring exercise desired to be mimicked;
(iv) transmitting an electrobiomimetic stimulus comprising the selected time varying EMFP signals from said energy transmitting element; and
(v) transmitting said electrobiomimetic stimulus to target cells within said portion of tissue until growth characteristics of said cells and tissue are altered as compared to cells and tissue not receiving said stimulus.

In a fourth aspect, the present invention provides a system to treat tissue in vivo, the system comprising: an energy source; an energy transmitting element for providing an electrobiomimetic stimulus; and a holding mechanism adapted to hold tissue, such that electrobiomimetic stimulus emitted by said energy transmitting element treats said tissue.

In a fifth aspect, the present invention provides a method of treating an individual comprising the steps of:
(i) providing a device comprising an electromagnetic field pulse generator;
(ii) positioning the device adjacent to a bodily tissue of an individual;
(iii) selecting a pattern of specifically configured time varying EMFP signals according to the type of physical exercise and associated bioelectrical effects produced by cells and tissue during exercise desired to be mimicked; and
(iv) operating the device for a duration, at a frequency, and at a peak effective to elicit a therapeutic response in the individual, wherein the device is positioned relative to the individual such that the device induces an electrobiomimetic stimulus within the bodily tissue.

Preferably, the individual has a bone, joint, soft-tissue, or connective tissue disorder and the therapeutic response comprises a reduction or elimination of inflammation and/or pain in a bone, joint, soft-tissue, or connective tissue of the individual.

Preferably, the individual has a disorder selected from the group consisting of adhesive capsulitis, tennis elbow, osteoarthritis, back pain, multiple sclerosis, tendon inflammation, and carpal tunnel syndrome, and the therapeutic response comprises a reduction or elimination of inflammation and/or pain associated with the disorder.

DETAILED DESCRIPTION OF THE PREFERRED EMBODIMENTS

Figure 1:
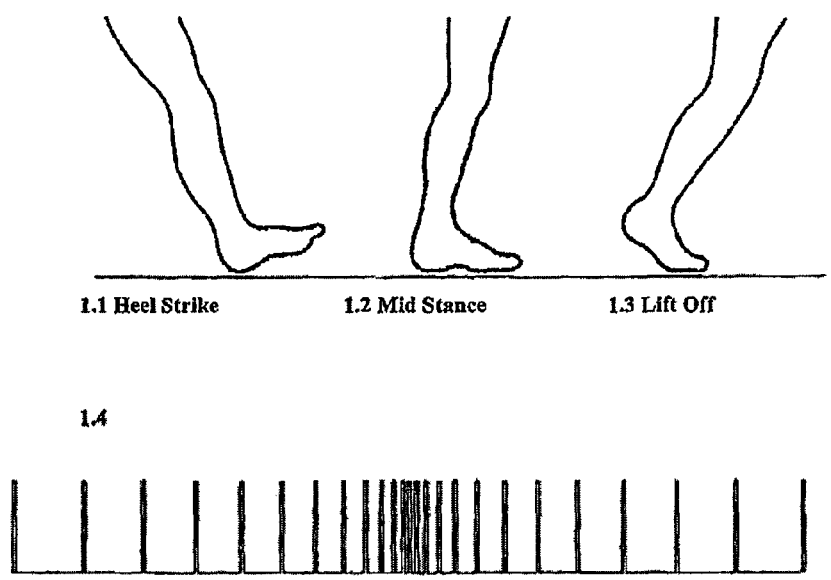
FIG. 1 is a graphical representation of the bioelectrical events recorded in dynamically loaded bone during normal articulation at walking frequencies of less than 1 cycle per second and with an applied load dynamic of less that 1.5 times body weight.

Before describing the present invention in detail, it is to be understood that this invention is not limited to particularly exemplified cell culture techniques, serum, media or methods and may, of course, vary. It is also to be understood that the terminology used herein is for the purpose of describing particular embodiments of the invention only, and is not intended to be limiting which will be limited only by the appended claims.

All publications, patents and patent applications cited herein, whether supra or infra, are hereby incorporated by reference in their entirety. However, publications mentioned herein are cited for the purpose of describing and disclosing the protocols, reagents and vectors which are reported in the publications and which might be used in connection with the invention. Nothing herein is to be construed as an admission that the invention is not entitled to antedate such disclosure by virtue of prior invention.

It must be noted that as used herein and in the appended claims, the singular forms "a," "an," and "the" include plural reference unless the context clearly dictates otherwise. Thus, for example, a reference to "a cell" includes a plurality of such cells, and a reference to "an electrobiomimetic pulse" is a reference to one or more pulses, and so forth. Unless defined otherwise, all technical and scientific terms used herein have the same meanings as commonly understood by one of ordinary skill in the art to which this invention belongs. Although any materials and methods similar or equivalent to those described herein can be used to practice or test the present invention, the preferred materials and methods are now described.

The broadest aspect of the present invention relates to a method for stimulating cells and tissue in vivo by applying an electrobiomimetic stimulus.

The term "in vivo" as used herein specifically refers to the stimulation of cells and tissue within the body of an individual or animal. The terms "stimulation" and "stimulating" as used herein interchangeably means that the electrobiomimetic stimulus affects the cells or tissue of the animal such that the "growth characteristics" of these cells are enhanced relative to cells or tissue not stimulated by the electrobiomimetic stimulus of the present invention. The enhanced growth of cells and tissue can be readily determined by persons skilled in the art.

The term "electrobiomimetic stimulus" as used herein refers to a time varying stimulus that is produced by an electromagnetic field pulse, which mimics the bioelectrical effects produced by cells and tissue during real physical exercise.

It will be appreciated by those skilled in the art that the electrobiomimetic stimulus comprising an electromagnetic field pulse (EMFP) can be of any magnetic field intensity so long as it provides an alteration in the growth characteristics of in vitro cultured cells. In some embodiments, the magnetic field intensity is between about 1 Gauss to about 100 Gauss i.e. between 0.00111 T to 11.12, preferably 3 gauss and of such flux as to induce between 1.0 and 2.0 my/cm, preferably 1.4 my/cm of free standing conductor.

In this regard, it should be noted that the International System (SI) unit of field intensity for magnetic fields is Tesla (T). One tesla (1 T) is defined as the field intensity generating one newton of force per ampere of current per meter of conductor:

$$T = Nw \cdot A^{-1} \cdot m^{-1} = kg \cdot s^{-2} \cdot A^{-1}$$

However, certain other non-SI units, like Gauss (G), are interchangeably used herein. Some are important for the interpretation of older scientific texts, but their use is not encouraged. Table 1 shows the conversion factors from one unit to another:

| Tesla (T) | Microtesla (μT) | Gauss (G) | Miligauss (mG) |
|---|---|---|---|
| 1 | 1000000 | 10000 | 10000000 |
| 0.000001 | 1 | 1000 | 10 |
| 0.0001 | 0.001 | 1 | 1000 |
| 0.0000001 | 0.01 | 0.001 | 1 |

The term "time varying" as used herein refers to the phenomena where the patterns of electrobiomimetic stimulus are delivered to the cells, tissue and organs in situ for varying lengths of time depending upon the requirements for the treatment.

The present invention functions through the stimulation of specific and predictable bioresponse in the major joints of an individual's body through the simulation of the bio-electro-phenomena induced in connective tissues by real physical activity.

In order to provide the optimum biomimetic stimuli to encourage the resolution of common injury and overuse pathologies in various joints and tissue groups of the body, specifically configured time varying electromagnetic fields pulses have been developed by the present inventors to mimic those produced in those tissue groups by exercise of the maximum benefited nature.

As described supra and infra, the electrobiomimetic stimulus comprises a number of time periods comprising blocks of electromagnetic field pulse, which are distinct from each other. These time periods are designed to mimic the typical exercise pattern of "warm up", "maximal exercise" and "cool down". In some embodiments, the time periods simulating a gentle walk (period 1), explosive exercise (period 2) and then light jog (period 3), wherein the rate or frequency of delivery of the blocks of electromagnetic field pulse plays an important role.

The duration of each time period will be tailored to the desired result. For example, as described in examples 1 to 12 infra, different joints, body parts and like will require slightly different time periods. However, generally there are three time periods, where the first time period (period 1) has duration of between 2 minutes and 9 minutes, the second time period (period 2) has a duration of between 10 minutes and 18 minutes and the third time period (period 3) has a duration between 6 minutes and 12 minutes.

The electromagnetic field pulse blocks or "patterns" within each time period can also vary. The electronicmagnetic field pulse blocks are designed to replicate the piezo-electric response observed in fully hydrated connective tissues, when subjected to normal physiological stress levels. Each electromagnetic field pulse block is separated by an interval of no electromagnetic field pulse. The interval separating the electromagnetic field pulse blocks will be of variable time lengths depending upon the treatment requirements. In some embodiments, the interval between each electromagnetic field pulse block in period 1 will be between 14 ms and 200 ms, while the interval in period 2 will be between 5 ms and 80 ms and the interval in period 3 between 20 ms and 100 ms.

Once a particular treatment regime has been devised an individual is treated using the electrobiomimetic stimuli. The term "individual" as used herein refers to any member of the class mammalia, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs. The terms do not denote a particular age. Thus, both adult and newborn individuals are intended to be covered.

Thus, provided is the treatment of mammals such as humans, as well as those mammals of economical importance and/or social importance to humans, for instance, carnivores other than humans (such as cats and dogs), swine (pigs, hogs, and wild boars), ruminants (such as cattle, oxen, sheep, giraffes, deer, goats, bison, and camels), and horses.

Generally, the terms "treating," "treatment, "healing" and the like are used herein to mean affecting an individual or subject, their tissue or cells to obtain a desired pharmacological and/or physiological effect. The effect is generally therapeutic in terms of partial or complete cure of a bone, joint, soft-tissue, or connective tissue disorder. "Treating" as used herein covers any treatment of disorder in a mammal, particularly a human, and includes: (a) inhibiting the progression of a bone, joint, soft-tissue, or connective tissue disorder, i.e., arresting its development; or (b) relieving or ameliorating the symptoms of a bone, joint, soft-tissue, or connective tissue disorder, i.e., cause regression of 10 the symptoms of the disorder.

In particular, the therapeutic response will comprise a reduction or elimination of inflammation and/or pain associated with a bone, joint, soft-tissue, or connective tissue of the individual. This will partially be brought about by an enhancement of the growth of cells and tissue.

In some embodiments, the disorder is selected from the group consisting of adhesive capsulitis, tennis elbow, osteoarthritis, back pain, multiple sclerosis, tendon inflammation, and carpal tunnel syndrome, and the therapeutic response comprises a reduction or elimination of inflammation and/or pain associated with the disorder.

Throughout the description and claims of this specification, the word "comprise" and variations of the word, such as "comprising" and comprises", is not intended to excluded other additives, components, integers or steps.

The invention will now be further described by way of reference only to the following non-limiting figures. It should be understood, however, that the description following is illustrative only, and should not be taken in any way as a restriction on the generality of the invention described above.

Now Referring to FIG. 1, there is illustrated, a leg of a normal adult through the stagers of normal ambulation gait in which 1.1 represents the heel strike phase, 1.2 represents the weight transition phase and 1.3 represents the lift-off phase. 1.4 is a graphical representation of the relative changes in frequency of resonance of bioelectrical phenomena observed in the leg during ambulation.

The forces of compression applied to the leg vary during the phases of progression within the gait and these forces act to modify the normal frequency of resonance. As physiological processes such as osteogenesis are known to be stimulated by such ambulation the bioresponse observed must dependent on presence of such bioelectrical phenomena and not on a fixed standing stimuli as proposed by McLeod et al in U.S. Pat. No. 5,318,561 and Markoll in U.S. Pat. No. 5,453,073.

Additionally, the frequency of resonance of bioelectrical phenomena observed in children are distinctly different from those observed in adults, yet it is well known that physiological processes such as osteogenesis are stimulated by the same real physical exercise. Evidence of such physiological processes being stimulating by such widely varying bioelectrical phenomena indicate that the simple stimuli model of the standing or non varying wave form do not replicate the complex nature of biomimetic phenomena and that only complex stimuli, as disclosed, are capable of mimicking actual bioelectrical phenomena.

Figure 2:
FIG. 2 is a graphical representation of the bioelectrical events that take place in the region of the tibia in a normal adult during the stages of ambulation.
Figure 2:
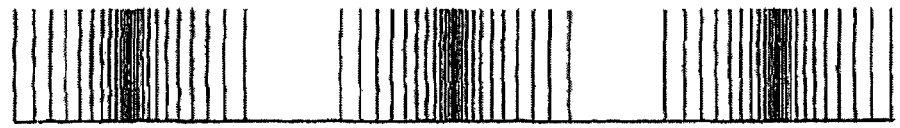
Figure 2:

Now referring to FIG. 2, there is illustrated the bioelectrical phenomena observed in different types of ambulation.

2.1 illustrates the typical adult walk of 1 stride or cycle per second during which a load influence of approximately 1.5 times body weight is applied and acts to stimulate physiological processes.

It is generally known that walking, producing the combinatorial patterns of bioelectrical phenomena of described in 2.1 stimulates a number of beneficial physiological processes including the dilation of blood vessels, the masking or modification of the inflammatory response, the opening of various ATP channels and the release of certain precursor hormones and chemical messengers.

2.2 illustrates the bioelectrical phenomena observed in adults in response to a jogging form of ambulation. In the illustrated case, a stride or cycle rate of 0.8 cycles per second is used and a compressive force equal to approximately 2.0 times body weight. Such combinatorial patterns are known to produce physiological effects including but not limited to, the eneration of aligning forces that assist in the organization of newly synthesized biomaterials, the suppression of the immune response and a relaxation of the metabolic water-binding forces.

2.3 illustrates the bioelectrical phenomena observed in adults in response to a running form of ambulation. In the illustrated case, a stride or cycle rate of 2.3 cycles per second is used and a compressive force equal to approximately 3.0 times body weight. Such complex combinatorial stimuli patterns are know to stimulate biosynthesis across a range of tissues and at rates statistically higher than with other complex stimuli patterns.

Figure 3:
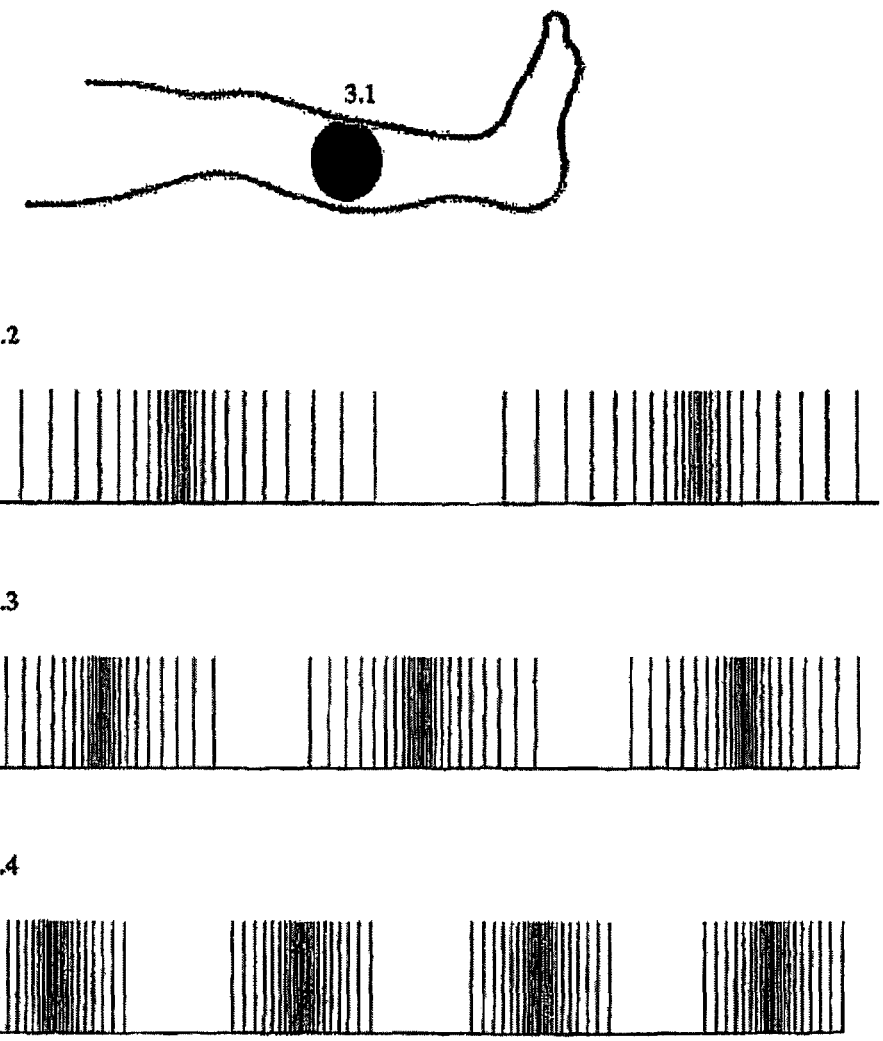
FIG. 3 is a graphical representation of combinatorial stimuli of bioelectrotherapy signals and other physical parameters applied as a biomimicry signal for the purposes of stimulating specific beneficial processes.

Now referring to FIG. 3, there is illustrated a form of applied biomimicry in which complex combinatorial forms of electrotherapy, possibly, but not essentially, of a time varying electromagnetic type with a combination of changes in environmental physical parameters such as, but not limited to, temperature, pressure and humidity, are applied to evoke and elicit complex beneficial physiological processes.

3.2 illustrates one possible bioelectromimetic type, applied as a biomimicry signal for the purposes of stimulating the dilation of blood vessels, the masking or modification of the inflammatory response, the opening of the various ATP channels and the release of certain precursor hormones and chemical messengers without the cellular trauma and tissue damage associated with real physical exercise.

3.3 illustrates one possible bioelectromimetic form applied as a biomimicry signal for the purposes of stimulating organizational influences for the alignment of newly synthesized biomaterials, the suppression of the immune response and a relaxation of the metabolic water-binding forces without the cellular trauma and tissue damage associated with real physical exercise.

3.4 illustrates one possible bioelectromimetic form applied as a biomimicry signal for the purposes of stimulating biosynthesis without the cellular trauma and tissue damage associated with real physical exercise.

Further details of practicing this inventive subject matter are furnished by way of the following examples which, however, should not be construed so as to imposes any kind of limitation to the scope of the invention.

EXAMPLE 1

Treatment of Ankles

The ankle is subject to specific loads during normal articulation. In order to provide the healthiest physiology to encourage rapid tissue turn-over, electrobiomimetic stimulus was applied as follows:

| | |
|---|---|
| Period 1 Duration | 8 minutes |
| Period 2 Duration | 10 minutes |
| Period 3 Duration | 12 minutes |
| Period 1 Interval | 40 ms |
| Period 2 Interval | 20 ms |
| Period 3 Interval | 50 ms |
| Pulse Duration | 300 µs |
| P1 × 100 µs | 200 |
| P2 × 100 µs | 100 |
| P3 × 100 µs | 80 |
| P4 × 100 µs | 60 |
| P5 × 100 µs | 40 |
| P6 × 100 µs | 20 |
| P7 × 100 µs | 10 |
| P8 × 100 µs | 5 |
| P9 × 100 µs | 5 |
| P10 × 100 µs | 5 |
| P11 × 100 µs | 5 |
| P12 × 100 µs | 40 |
| P13 × 100 µs | 60 |
| P14 × 100 µs | 100 |
| P15 × 100 µs | 120 |
| P16 × 100 µs | 120 |
| P17 × 100 µs | 140 |
| P18 × 100 µs | 160 |
| P19 × 100 µs | 200 |
| P20 × 100 µs | 200 |

Figure 4:
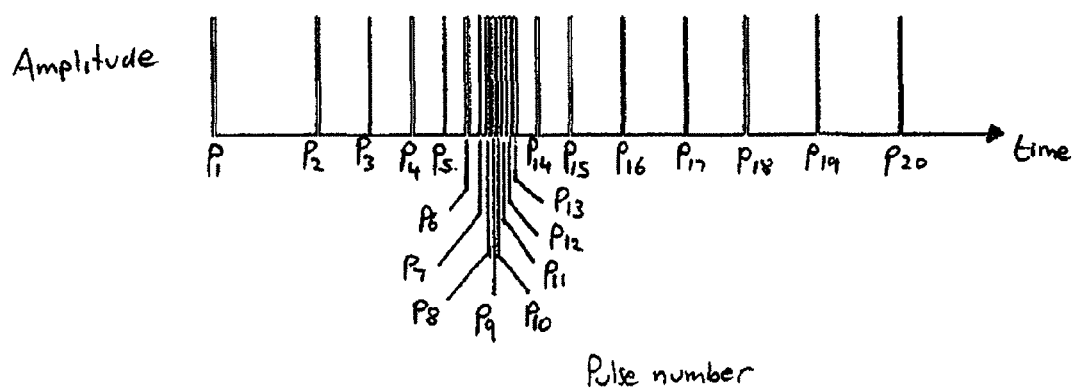
FIG. 4 shows a pictorially representation of a treatment regime for the treatment of an ankle injury.

The regime described above is shown pictorially in FIG. 4.

EXAMPLE 2

Treatment of Bones

Bone is subject to constant and continuous remodelling and osteogenesis is known to be stimulated by exercise. In order to provide the healthiest physiology to encourage rapid bone-growth, electrobiomimetic stimulus was applied as follows:

| | |
|---|---|
| Period 1 Duration | 2 minutes |
| Period 2 Duration | 18 minutes |
| Period 3 Duration | 10 minutes |
| Period 1 Interval | 90 ms |
| Period 2 Interval | 40 ms |
| Period 3 Interval | 100 ms |
| Pulse Duration | 300 µs |
| P1 × 100 µs | 4 |
| P2 × 100 µs | 4 |
| P3 × 100 µs | 4 |
| P4 × 100 µs | 4 |
| P5 × 100 µs | 4 |
| P6 × 100 µs | 4 |
| P7 × 100 µs | 4 |
| P8 × 100 µs | 4 |
| P9 × 100 µs | 4 |
| P10 × 100 µs | 50 |
| P11 × 100 µs | 50 |
| P12 × 100 µs | 50 |
| P13 × 100 µs | 50 |
| P14 × 100 µs | 50 |
| P15 × 100 µs | 50 |
| P16 × 100 µs | 50 |
| P17 × 100 µs | 50 |
| P18 × 100 µs | 50 |
| P19 × 100 µs | 50 |
| P20 × 100 µs | 50 |

Figure 5:
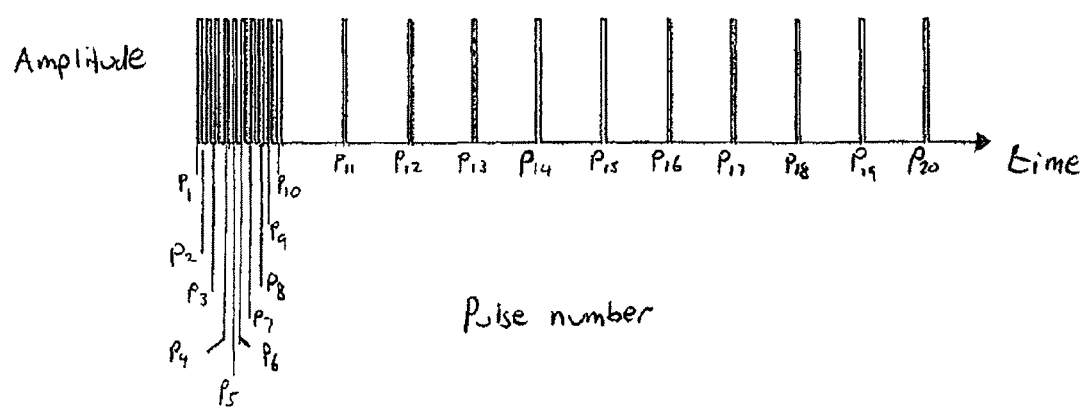
FIG. 5 shows a pictorially representation of a treatment regime for the treatment of bone disorders.

The regime described above is shown pictorially in FIG. 5.

EXAMPLE 3

Treatment of Elbow

The elbow is subject to both overuse and traumatic injuries and combines a range of tissue groups. In order to provide the healthiest physiology to encourage rapid repair and reductions in inflammation, electrobiomimetic stimulus was applied as follows:

| | |
|---|---|
| Period 1 Duration | 3 minutes |
| Period 2 Duration | 17 minutes |
| Period 3 Duration | 10 minutes |
| Period 1 Interval | 100 ms |
| Period 2 Interval | 14 ms |
| Period 3 Interval | 75 ms |
| Pulse Duration | 300 µs |
| P1 × 100 µs | 255 |
| P2 × 100 µs | 200 |
| P3 × 100 µs | 100 |
| P4 × 100 µs | 90 |
| P5 × 100 µs | 80 |
| P6 × 100 µs | 70 |
| P7 × 100 µs | 60 |
| P8 × 100 µs | 50 |
| P9 × 100 µs | 40 |
| P10 × 100 µs | 30 |
| P11 × 100 µs | 10 |
| P12 × 100 µs | 11 |
| P13 × 100 µs | 9 |
| P14 × 100 µs | 8 |
| P15 × 100 µs | 7 |
| P16 × 100 µs | 6 |
| P17 × 100 µs | 5 |
| P18 × 100 µs | 4 |
| P19 × 100 µs | 3 |
| P20 × 100 µs | 2 |

Figure 6:
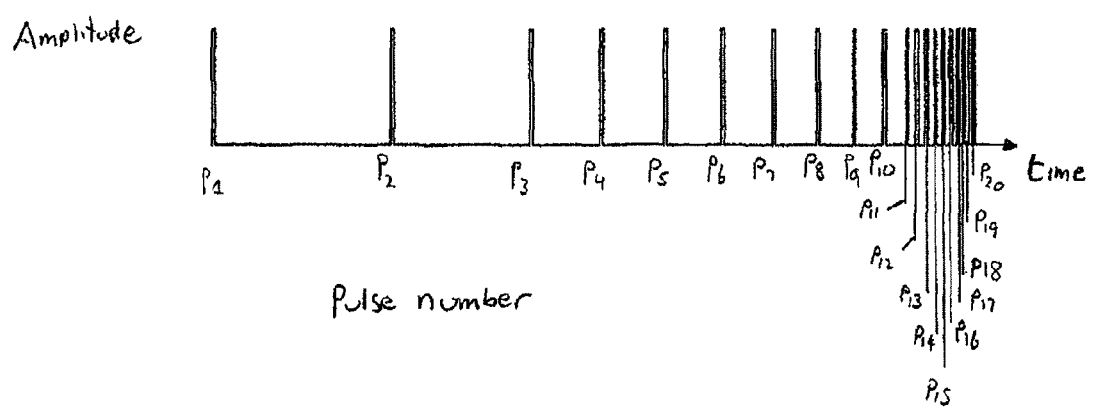
FIG. 6 shows a pictorially representation of a treatment regime for the treatment of tennis elbow.

The regime described above is shown pictorially in FIG. 6.

EXAMPLE 4

Treatment of Hip Injury

The hip is a complex joint subject to stresses primarily in the vertical plane. The hip is subject to both degeneration as well as trauma including connective tissues and articular surfaces. In order to provide the healthiest physiology to encourage rapid repair and reductions in inflammation, electrobiomimetic stimulus was applied as follows:

| | |
|---|---|
| Period 1 Duration | 8 minutes |
| Period 2 Duration | 12 minutes |
| Period 3 Duration | 10 minutes |
| Period 1 Interval | 35 ms |
| Period 2 Interval | 5 ms |
| Period 3 Interval | 50 ms |
| Pulse Duration | 220 µs |
| P1 × 100 µs | 200 |
| P2 × 100 µs | 200 |
| P3 × 100 µs | 200 |
| P4 × 100 µs | 200 |
| P5 × 100 µs | 200 |
| P6 × 100 µs | 200 |
| P7 × 100 µs | 180 |
| P8 × 100 µs | 160 |
| P9 × 100 µs | 140 |
| P10 × 100 µs | 120 |
| P11 × 100 µs | 100 |
| P12 × 100 µs | 80 |
| P13 × 100 µs | 60 |

-continued

| | |
|---|---|
| P14 × 100 μs | 40 |
| P15 × 100 μs | 20 |
| P16 × 100 μs | 10 |
| P17 × 100 μs | 0 |
| P18 × 100 μs | 0 |
| P19 × 100 μs | 0 |
| P20 × 100 μs | 0 |

Figure 7:
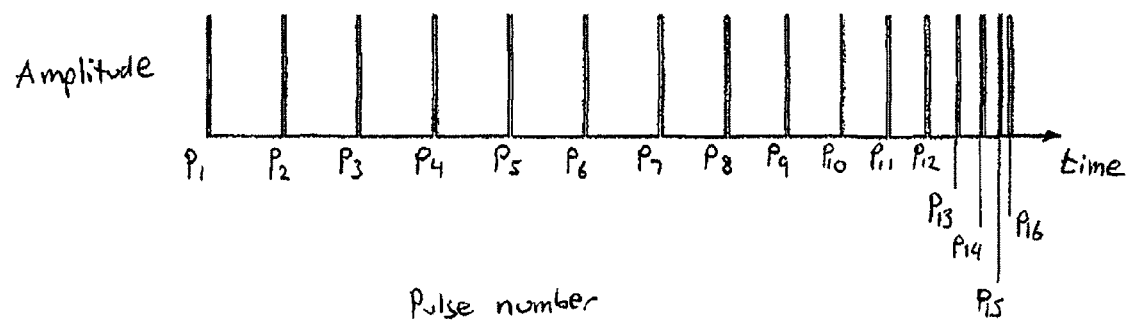
FIG. 7 shows a pictorially representation of a treatment regime for the treatment of hip injury.

The regime described above is shown pictorially in FIG. 7.

EXAMPLE 5

Treatment of Knee Injury

The knee is subject to multiple injuries which can often be made more severe by degeneration, pain and loss of mobility. In order to provide the healthiest physiology to encourage rapid repair and reductions in inflammation, electrobiomimetic stimulus was applied as follows:

| | |
|---|---|
| Period 1 Duration | 2 minutes |
| Period 2 Duration | 18 minutes |
| Period 3 Duration | 10 minutes |
| Period 1 Interval | 200 ms |
| Period 2 Interval | 80 ms |
| Period 3 Interval | 250 ms |
| Pulse Duration | 200 μs |
| P1 × 100 μs | 255 |
| P2 × 100 μs | 240 |
| P3 × 100 μs | 220 |
| P4 × 100 μs | 200 |
| P5 × 100 μs | 180 |
| P6 × 100 μs | 100 |
| P7 × 100 μs | 50 |
| P8 × 100 μs | 20 |
| P9 × 100 μs | 10 |
| P10 × 100 μs | 5 |
| P11 × 100 μs | 1 |
| P12 × 100 μs | 5 |
| P13 × 100 μs | 20 |
| P14 × 100 μs | 50 |
| P15 × 100 μs | 80 |
| P16 × 100 μs | 100 |
| P17 × 100 μs | 150 |
| P18 × 100 μs | 200 |
| P19 × 100 μs | 210 |
| P20 × 100 μs | 220 |

Figure 8:
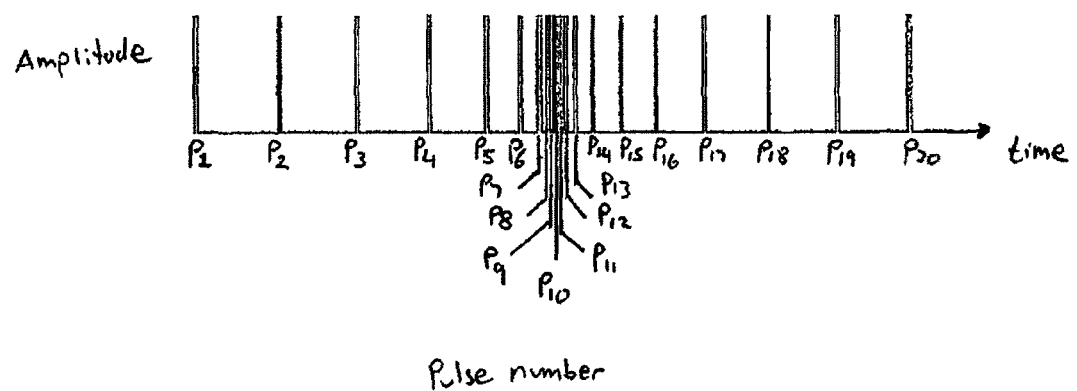
FIG. 8 shows a pictorially representation of a treatment regime for the treatment of knee injury.

The regime described above is shown pictorially in FIG. 8.

EXAMPLE 6

Treatment of Lower Back Strain

The lower back is subject to both acute and chronic conditions involving overuse injury, trauma and degenerative conditions. In order to provide the healthiest physiology to encourage rapid repair and reductions in inflammation, electrobiomimetic stimulus was applied as follows:

| | |
|---|---|
| Period 1 Duration | 8 minutes |
| Period 2 Duration | 12 minutes |
| Period 3 Duration | 10 minutes |
| Period 1 Interval | 35 ms |
| Period 2 Interval | 5 ms |
| Period 3 Interval | 50 ms |
| Pulse Duration | 220 μs |
| P1 × 100 μs | 1 |

-continued

| | |
|---|---|
| P2 × 100 μs | 10 |
| P3 × 100 μs | 20 |
| P4 × 100 μs | 40 |
| P5 × 100 μs | 80 |
| P6 × 100 μs | 120 |
| P7 × 100 μs | 160 |
| P8 × 100 μs | 200 |
| P9 × 100 μs | 220 |
| P10 × 100 μs | 240 |
| P11 × 100 μs | 255 |
| P12 × 100 μs | 240 |
| P13 × 100 μs | 220 |
| P14 × 100 μs | 200 |
| P15 × 100 μs | 160 |
| P16 × 100 μs | 0 |
| P17 × 100 μs | 0 |
| P18 × 100 μs | 0 |
| P19 × 100 μs | 0 |
| P20 × 100 μs | 0 |

Figure 9:
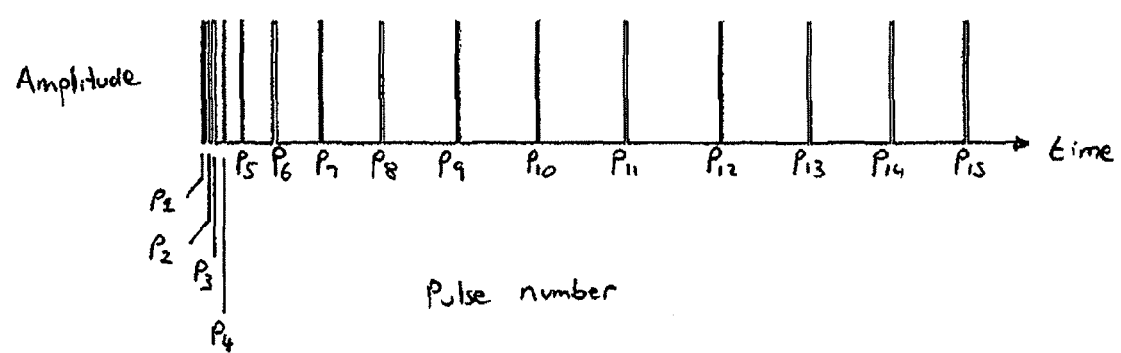
FIG. 9 shows a pictorially representation of a treatment regime for the treatment of lower back strain.

The regime described above is shown pictorially in FIG. 9.

EXAMPLE 7

Treatment of Mid Back Strain

The Mid Back region is subject to connective tissue degeneration as well as postural overuse conditions that are often chronic in nature. In order to provide the healthiest physiology to encourage rapid repair and reductions in inflammation, electrobiomimetic stimulus was applied as follows:

| | |
|---|---|
| Period 1 Duration | 9 minutes |
| Period 2 Duration | 15 minutes |
| Period 3 Duration | 6 minutes |
| Period 1 Interval | 70 ms |
| Period 2 Interval | 5 ms |
| Period 3 Interval | 50 ms |
| Pulse Duration | 380 μs |
| P1 × 100 μs | 4 |
| P2 × 100 μs | 4 |
| P3 × 100 μs | 4 |
| P4 × 100 μs | 4 |
| P5 × 100 μs | 4 |
| P6 × 100 μs | 4 |
| P7 × 100 μs | 20 |
| P8 × 100 μs | 40 |
| P9 × 100 μs | 80 |
| P10 × 100 μs | 100 |
| P11 × 100 μs | 120 |
| P12 × 100 μs | 180 |
| P13 × 100 μs | 200 |
| P14 × 100 μs | 220 |
| P15 × 100 μs | 0 |
| P16 × 100 μs | 0 |
| P17 × 100 μs | 0 |
| P18 × 100 μs | 0 |
| P19 × 100 μs | 0 |
| P20 × 100μ | 0 |

Figure 10:
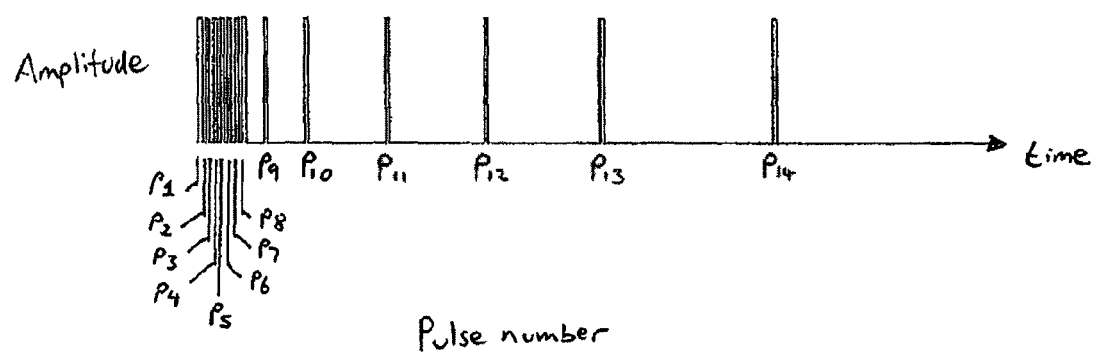
FIG. 10 shows a pictorially representation of a treatment regime for the treatment of mid back strain.

The regime described above is shown pictorially in FIG. 10.

EXAMPLE 8

Treatment of Neck Strain

The neck is a complex organ that is subject to overuse and traumatic conditions involving a range of musculo-tendinus insertions as well as tendo-osseous insertion point 10 disorders. Degeneration and trauma top the articular surfaces can also playa role in Neck pathologies. In order to provide the healthiest physiology to encourage rapid repair and reductions in inflammation, electrobiomimetic stimulus was applied as follows:

| | |
|---|---|
| Period 1 Duration | 8 minutes |
| Period 2 Duration | 12 minutes |
| Period 3 Duration | 10 minutes |
| Period 1 Interval | 40 ms |
| Period 2 Interval | 25 ms |
| Period 3 Interval | 50 ms |
| Pulse Duration | 220 µs |
| P1 × 100 µs | 200 |
| P2 × 100 µs | 200 |
| P3 × 100 µs | 200 |
| P4 × 100 µs | 200 |
| P5 × 100 µs | 200 |
| P6 × 100 µs | 200 |
| P7 × 100 µs | 200 |
| P8 × 100 µs | 20 |
| P9 × 100 µs | 40 |
| P10 × 100 µs | 100 |
| P11 × 100 µs | 120 |
| P12 × 100 µs | 180 |
| P13 × 100 µs | 200 |
| P14 × 100 µs | 220 |
| P15 × 100 µs | 240 |
| P16 × 100 µs | 0 |
| P17 × 100 µs | 0 |
| P18 × 100 µs | 0 |
| P19 × 100 µs | 0 |
| P20 × 100µ | 0 |

Figure 11:
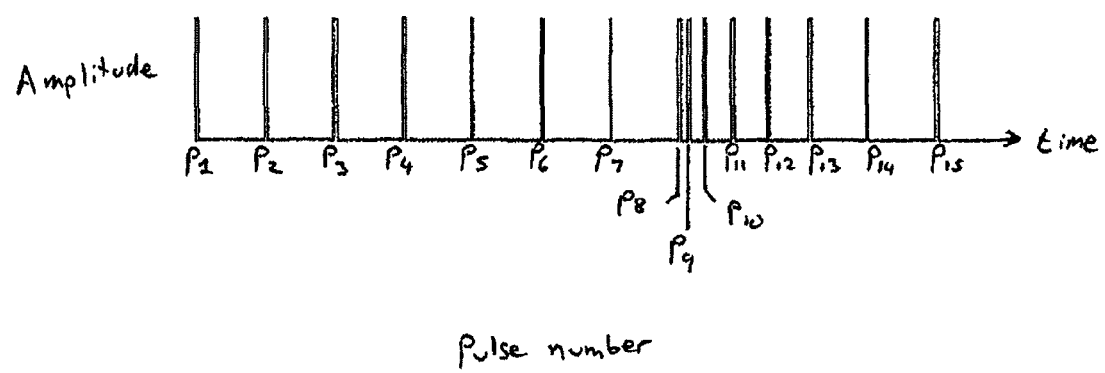
FIG. 11 shows a pictorially representation of a treatment regime for the treatment of neck strain.

The regime described above is shown pictorially in FIG. 11.

EXAMPLE 9

Treatment of Osteoarthritis

Osteoarthritis is a degenerative disease that may affect any number of joints or regions of the body. The underling pathology usually involves the loss of articular surface due to a loss of balance between matrix formation and degeneration. In order to provide the healthiest physiology to encourage rapid repair and reductions in inflammation, electrobiomimetic stimulus was applied as follows:

| | |
|---|---|
| Period 1 Duration | 5 minutes |
| Period 2 Duration | 15 minutes |
| Period 3 Duration | 10 minutes |
| Period 1 Interval | 40 ms |
| Period 2 Interval | 20 ms |
| Period 3 Interval | 50 ms |
| Pulse Duration | 200 µs |
| P1 × 100 µs | 50 |
| P2 × 100 µs | 25 |
| P3 × 100 µs | 3 |
| P4 × 100 µs | 3 |
| P5 × 100 µs | 3 |
| P6 × 100 µs | 3 |
| P7 × 100 µs | 3 |
| P8 × 100 µs | 3 |
| P9 × 100 µs | 3 |
| P10 × 100 µs | 3 |
| P11 × 100 µs | 3 |
| P12 × 100 µs | 3 |
| P13 × 100 µs | 3 |
| P14 × 100 µs | 3 |
| P15 × 100 µs | 3 |
| P16 × 100 µs | 0 |
| P17 × 100 µs | 0 |
| P18 × 100 µs | 0 |
| P19 × 100 µs | 0 |
| P20 × 100µ | 0 |

Figure 12:
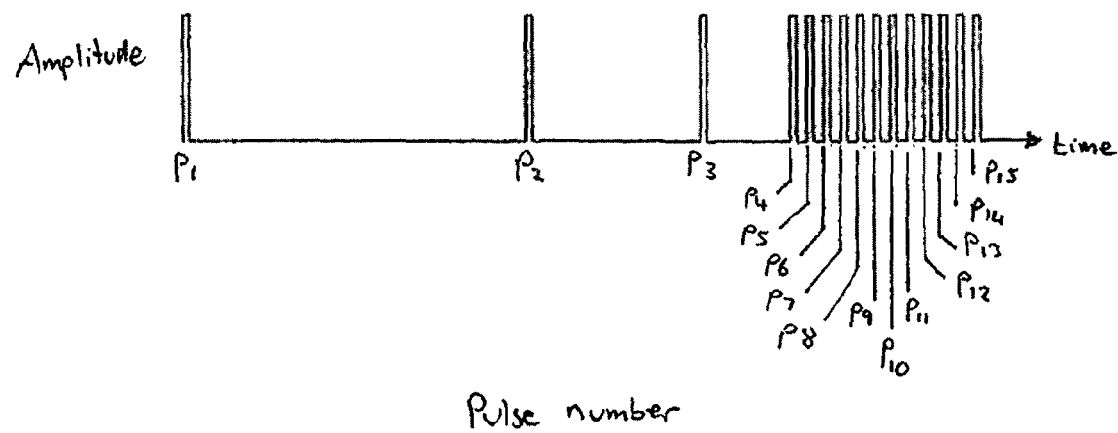
FIG. 12 shows a pictorially representation of a treatment regime for the treatment of osteoarthritis.

The regime described above is shown pictorially in FIG. 12.

EXAMPLE 10

Treatment of Shoulder Injury

The shoulder often presents with chronic overuse syndromes, which can limit range of motion and dramatically reduce quality of life. The shoulder is subject to overuse and traumatic conditions involving a range of musculo-tendinus insertions as well as tendo-osseous insertion point disorders and can also involve osteoporosis and other bone related syndromes. In order to provide the healthiest physiology to encourage rapid repair and reductions in inflammation, electrobiomimetic stimulus was applied as follows:

| | |
|---|---|
| Period 1 Duration | 8 minutes |
| Period 2 Duration | 12 minutes |
| Period 3 Duration | 10 minutes |
| Period 1 Interval | 35 ms |
| Period 2 Interval | 5 ms |
| Period 3 Interval | 50 ms |
| Pulse Duration | 200 µs |
| P1 × 100 µs | 1 |
| P2 × 100 µs | 10 |
| P3 × 100 µs | 20 |
| P4 × 100 µs | 40 |
| P5 × 100 µs | 80 |
| P6 × 100 µs | 120 |
| P7 × 100 µs | 160 |
| P8 × 100 µs | 200 |
| P9 × 100 µs | 220 |
| P10 × 100 µs | 240 |
| P11 × 100 µs | 220 |
| P12 × 100 µs | 20 |
| P13 × 100 µs | 40 |
| P14 × 100 µs | 60 |
| P15 × 100 µs | 80 |
| P16 × 100 µs | 100 |
| P17 × 100 µs | 0 |
| P18 × 100 µs | 0 |
| P19 × 100 µs | 0 |
| P20 × 100 µs | 0 |

Figure 13:
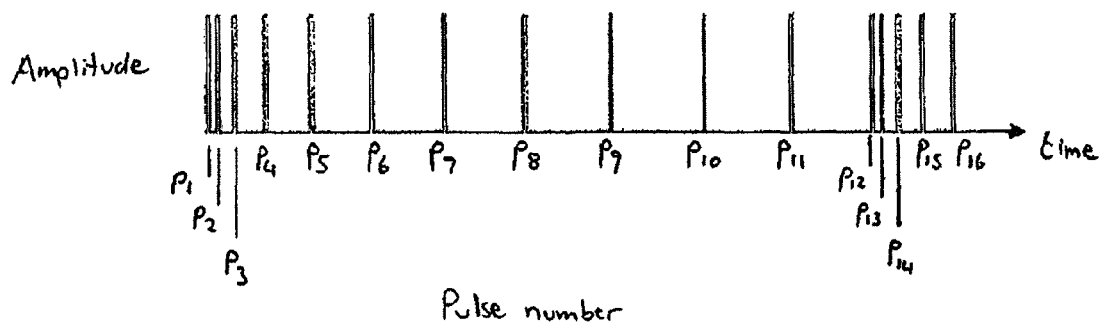
FIG. 13 shows a pictorially representation of a treatment regime for the treatment of a shoulder injury.

The regime described above is shown pictorially in FIG. 13.

EXAMPLE 11

Treatment of Vascular Disorders

Vascular insufficiency disorders are common in chronic musculo-skeletal conditions and can impact in the ability of the condition to resolve fully in the absence of a supporting capillary arcade. Vascular stimulation involving induced electro-osteogenesis can be particularly beneficial in such cases. In order to provide the healthiest physiology to encourage rapid repair and reductions in inflammation, electrobiomimetic stimulus was applied as follows:

| | |
|---|---|
| Period 1 Duration | 5 minutes |
| Period 2 Duration | 15 minutes |
| Period 3 Duration | 10 minutes |
| Period 1 Interval | 14 ms |
| Period 2 Interval | 10 ms |
| Period 3 Interval | 20 ms |
| Pulse Duration | 380 μs |
| P1 × 100 μs | 4 |
| P2 × 100 μs | 0 |
| P3 × 100 μs | 0 |
| P4 × 100 μs | 0 |
| P5 × 100 μs | 0 |
| P6 × 100 μs | 0 |
| P7 × 100 μs | 0 |
| P8 × 100 μs | 0 |
| P9 × 100 μs | 0 |
| P10 × 100 μs | 0 |
| P11 × 100 μs | 0 |
| P12 × 100 μs | 0 |
| P13 × 100 μs | 0 |
| P14 × 100 μs | 0 |
| P15 × 100 μs | 0 |
| P16 × 100 μs | 0 |
| P17 × 100 μs | 0 |
| P18 × 100 μs | 0 |
| P19 × 100 μs | 0 |
| P20 × 100 μs | 0 |

Figure 14:
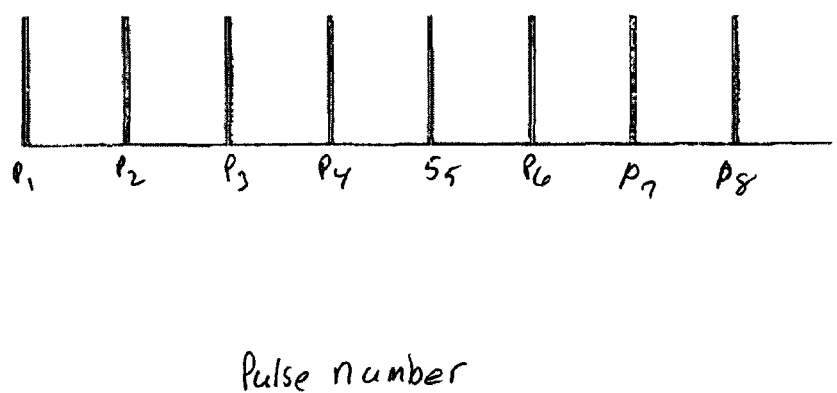
FIG. 14 shows a pictorially representation of a treatment regime for the treatment of a vascular disorder.

The regime described above is shown pictorially in FIG. 14.

EXAMPLE 12

Treatment of Wrist Injury

The wrist is highly mobile joint subject to many traumatic events and damaging influences. The wrist commonly presents with overuse and articular surface damage as well as bone and rheumatoid disorders. In order to provide the healthiest physiology to encourage rapid repair and reductions in inflammation, electrobiomimetic stimulus was applied as follows:

| | |
|---|---|
| Period 1 Duration | 8 minutes |
| Period 2 Duration | 12 minutes |
| Period 3 Duration | 10 minutes |
| Period 1 Interval | 35 ms |
| Period 2 Interval | 5 ms |
| Period 3 Interval | 50 ms |
| Pulse Duration | 220 μs |
| P1 × 100 μs | 200 |
| P2 × 100 μs | 200 |
| P3 × 100 μs | 200 |
| P4 × 100 μs | 200 |
| P5 × 100 μs | 10 |
| P6 × 100 μs | 20 |
| P7 × 100 μs | 40 |
| P8 × 100 μs | 80 |
| P9 × 100 μs | 120 |
| P10 × 100 μs | 140 |
| P11 × 100 μs | 160 |
| P12 × 100 μs | 200 |
| P13 × 100 μs | 220 |
| P14 × 100 μs | 0 |
| P15 × 100 Rs | 0 |
| P16 × 100 μs | 0 |
| P17 × 100 μs | 0 |
| P18 × 100 μs | 0 |
| P19 × 100 μs | 0 |
| P20 × 100 μs | 0 |

Figure 15:
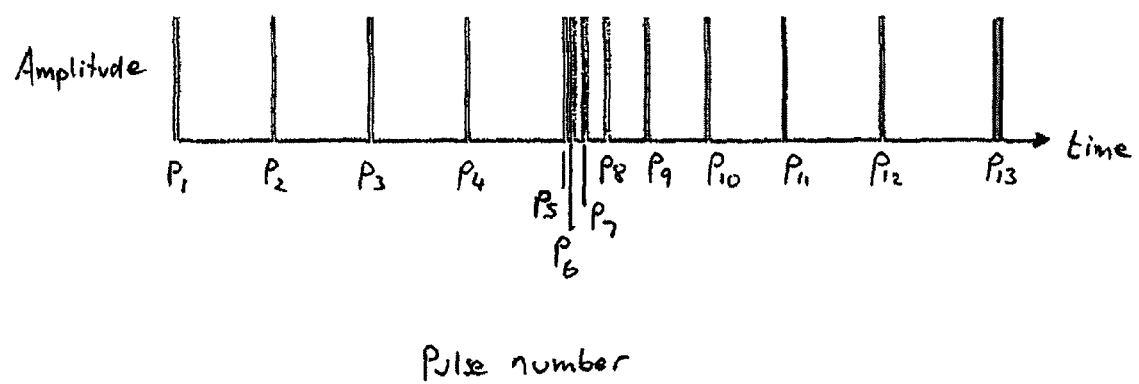
FIG. 15 shows a pictorially representation of a treatment regime for the treatment of a wrist injury.

The regime described above is shown pictorially in FIG. 15.

Figure 16:
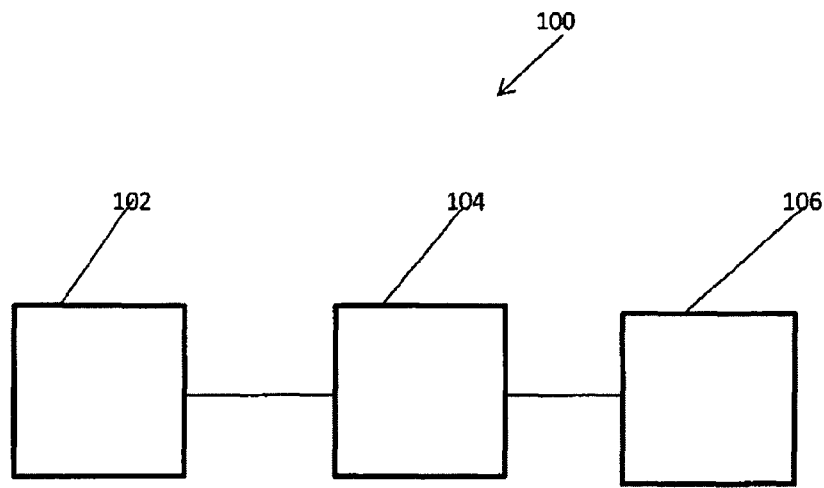
FIG. 16 is a schematic representation of a system capable of treating tissue in vivo in accordance with any of the treatment regimes depicted in FIGS. 4 to 15.

FIG. 16 depicts in block diagram form a system 100 for treating tissue in vivo. The system 100 comprises an energy source 102 which is electrically coupled to and provides electrical energy for an energy transmitting element 104 in the form of an electromagnetic field pulse (EMFP) generator. This generator produces the electrobiomimetic stimulus to the tissue. The transmitted element 104 is coupled with a holding mechanism 106 that is arranged to hold the tissue being treated. The holding mechanism is adapted so as to deliver the stimulus from the element 104 to the tissue whereby the tissue receives and is treated by the stimulus.

The invention claimed is:

1. A system to treat tissue in vivo, the system comprising:
   (i) an energy source;
   (ii) an energy transmitting element that provides an electrobiomimetic stimulus; and
   (iii) a holding mechanism adapted to hold tissue;
   wherein said energy transmitting element produces a pattern of specifically configured time varying electromagnetic field pulse signals according to a type of physical exercise desired to be mimicked and associated bioelectrical effects produced by cells and tissue during the type of physical exercise desired to be mimicked; wherein the time varying electromagnetic field pulse signals consist of a plurality of electromagnetic field pulse blocks separated by intervals of no electromagnetic field pulses, each electromagnetic field pulse block comprising a plurality of electromagnetic field pulses of defined duration, which pattern mimics the bioelectrical effects produced by cells and tissue during the type of physical exercise desired to be mimicked and wherein the electromagnetic field pulse signals have a magnetic field intensity of between 1 Gauss to 100 Gauss.

2. The system of claim 1, wherein said signal pattern comprises between 2 and 4 time periods, wherein each time period comprises said blocks of electromagnetic field pulses and wherein said blocks of electromagnetic field pulses are distinct from each other.

3. The system of claim 2, wherein each of the time periods simulate a gentle walk, explosive exercise and light jog, wherein a rate or frequency of delivery of the blocks of electromagnetic field pulses varies.

4. The system of claim 1, wherein said signal pattern comprises between 2 and 3 time periods, wherein each time period comprises said blocks of electromagnetic field pulses which are distinct from each other.

5. The system of claim 1, wherein said signal pattern comprises 3 time periods, wherein each time period comprises said blocks of electromagnetic field pulses which are distinct from each other.

6. The system of claim 1, wherein the electrobiomimetic stimulus comprises 3 time periods, wherein time period 1 has duration of between 2 minutes and 9 minutes, time period 2 has duration between 10 minutes and 18 minutes and time period 3 has duration between 6 minutes and 12 minutes.

7. The system of claim 1, wherein each of the intervals separating the electromagnetic field pulse blocks have variable time lengths.

8. The system of claim 7, wherein the interval between each electromagnetic field pulse block in a first period will be between 14 ms and 200 ms, while the interval in a second period 2 will be between 5 ms and 80 ms and the interval in a third period 3 will be between 20 ms and 100 ms.

9. The system of claim 8, wherein the magnetic field intensity is about 3 Gauss.

10. The system of claim 1, wherein the defined duration is between 200 μs and 380 μs.

11. The system of claim 1, wherein the number of electromagnetic field pulses in each block is between 1 and 50.

12. The system of claim 1, wherein the number of electromagnetic field pulses in each block is between 10 and 30.

13. The system of claim 1, wherein the number of electromagnetic field pulses in each block is about 20.

14. The system of claim 1, wherein the electromagnetic field pulse within each block is spaced by a varying time space.

15. The system of claim 14, wherein the varying time space between each electromagnetic field pulse is between 0 and 300000 µs.

\* \* \* \* \*

UNITED STATES PATENT AND TRADEMARK OFFICE
CERTIFICATE OF CORRECTION

PATENT NO. : 8,672,826 B2  
APPLICATION NO. : 12/296385  
DATED : March 18, 2014  
INVENTOR(S) : Edwards et al.

Page 1 of 1

It is certified that error appears in the above-identified patent and that said Letters Patent is hereby corrected as shown below:

On the Title Page, Item (54) and in the Specification, Column 1, lines 1-2, The title should read "IN VIVO STIMULATION OF CELLULAR MATERIAL"

Signed and Sealed this  
Twelfth Day of August, 2014

Michelle K. Lee  
*Deputy Director of the United States Patent and Trademark Office*

UNITED STATES PATENT AND TRADEMARK OFFICE
CERTIFICATE OF CORRECTION

PATENT NO. : 8,672,826 B2  Page 1 of 1
APPLICATION NO. : 12/296385
DATED : March 18, 2014
INVENTOR(S) : Edwards et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1405 days.

Signed and Sealed this
Twenty-ninth Day of September, 2015

Michelle K. Lee
*Director of the United States Patent and Trademark Office*